(12) United States Patent
Tu et al.

(10) Patent No.: US 8,801,629 B2
(45) Date of Patent: Aug. 12, 2014

(54) DUAL-WINGS PERCUTANEOUS NEEDLE

(76) Inventors: Hsien-Tang Tu, Taichung (TW);
Ming-Jen Chou, Taichung (TW);
Wing-Sheung Chan, Taichung (TW)

(*) Notice: Subject to any disclaimer, the term of this patent is extended or adjusted under 35 U.S.C. 154(b) by 697 days.

(21) Appl. No.: 13/084,049

(22) Filed: Apr. 11, 2011

(65) Prior Publication Data

US 2012/0259241 A1   Oct. 11, 2012

(51) Int. Cl.
*A61B 5/00* (2006.01)
*B65D 81/00* (2006.01)
*A61B 10/02* (2006.01)
*A61B 17/34* (2006.01)
*A61B 19/00* (2006.01)

(52) U.S. Cl.
CPC ....... *A61B 10/0233* (2013.01); *A61B 2019/202* (2013.01); *A61B 17/3403* (2013.01); *A61B 17/3421* (2013.01)
USPC .......................................................... 600/576

(58) Field of Classification Search
USPC ................ 600/562–583; 604/19, 21, 48; 606/181–182
See application file for complete search history.

(56) References Cited

U.S. PATENT DOCUMENTS

| 4,308,875 | A | * | 1/1982 | Young | 600/566 |
|---|---|---|---|---|---|
| 5,199,441 | A | * | 4/1993 | Hogle | 600/566 |
| 5,300,045 | A | * | 4/1994 | Plassche, Jr. | 604/263 |
| 5,316,013 | A | * | 5/1994 | Striebel et al. | 600/567 |
| 2005/0075580 | A1 | * | 4/2005 | Leigh et al. | 600/567 |

* cited by examiner

*Primary Examiner* — Rene Towa
(74) *Attorney, Agent, or Firm* — patenttm.us

(57) ABSTRACT

A dual-wings percutaneous needle has a sampling needle, an outer needle, a transverse position wing and a longitudinal position wing. The sampling needle has a length, a lower end and a needle head formed in the lower end of the sampling needle. The outer needle is hollow, is detachably mounted around the sampling needle and has a length shorter than the length of the sampling needle. The transverse position wing is lamellar, is stuck on the sampling needle or is stuck on the outer needle. The longitudinal position wing is lamellar, is stuck on the sampling needle adjacent to the transverse position wing and is perpendicular to the transverse position wing or is stuck on the outer needle adjacent to the transverse position wing and is perpendicular to the transverse position wing.

3 Claims, 5 Drawing Sheets

DUAL-WINGS PERCUTANEOUS NEEDLE

BACKGROUND OF THE INVENTION

1. Field of the Invention

The present invention relates to a percutaneous needle, and more particularly to a dual-wings percutaneous needle that can be operated precisely and easily.

2. Description of Related Art

Computed tomography is used to scan a patient for biopsy, and a specimen of tissue will be taken from the patient and be examined by a pathologist to check diseases, such as cancers. A doctor will take a specimen of tissue from the patient by puncturing a conventional percutaneous needle into a patient's body at a desired position, angle and depth determined by the computed tomography. A laser angle guide assembly that disclosed in Taiwan Patent No. M370388, in U.S. Pat. No. 7/806,592 B1 and in U.S. application Ser. No. 10/327,011 can be used to generate a transverse laser beam and a longitudinal laser beam to form an alternating spot on the desired position to help a doctor to puncture the needle assembly into the patient's body during the specimen process.

However, during the puncturing process, the angle of the conventional percutaneous needle cannot easily aim at the transverse laser beam and the longitudinal laser beam of the laser angle guide assembly at the same time so that the angle for the conventional percutaneous needle puncturing into the patient's body also has to be dependent on the experience and the intuition of the doctor. If the puncturing angle of the conventional percutaneous needle has a large deviation relative to the desired puncturing angle, this will cause pain to the patient and fail to take a specimen of tissue and even to lead complications to the patient.

To overcome the shortcomings, the present invention tends to provide a dual-wings percutaneous needle to mitigate or obviate the aforementioned problems.

SUMMARY OF THE INVENTION

The main objective of the invention is to provide a dual-wings percutaneous needle that can be operated precisely and easily.

The dual-wings percutaneous needle in accordance with the present invention has a sampling needle, an outer needle, a transverse position wing and a longitudinal position wing. The sampling needle has a length, a lower end and a needle head formed in the lower end of the sampling needle. The outer needle is hollow, is detachably mounted around the sampling needle and has a length shorter than the length of the sampling needle. The transverse position wing is lamellar, is stuck on the sampling needle or is stuck on the outer needle. The longitudinal position wing is lamellar, is stuck on the sampling needle adjacent to the transverse position wing and is perpendicular to the transverse position wing or is stuck on the outer needle adjacent to the transverse position wing and is perpendicular to the transverse position wing.

Other objects, advantages and novel features of the invention will become more apparent from the following detailed description when taken in conjunction with the accompanying drawings.

DETAILED DESCRIPTION OF PREFERRED EMBODIMENT

Figure 1:
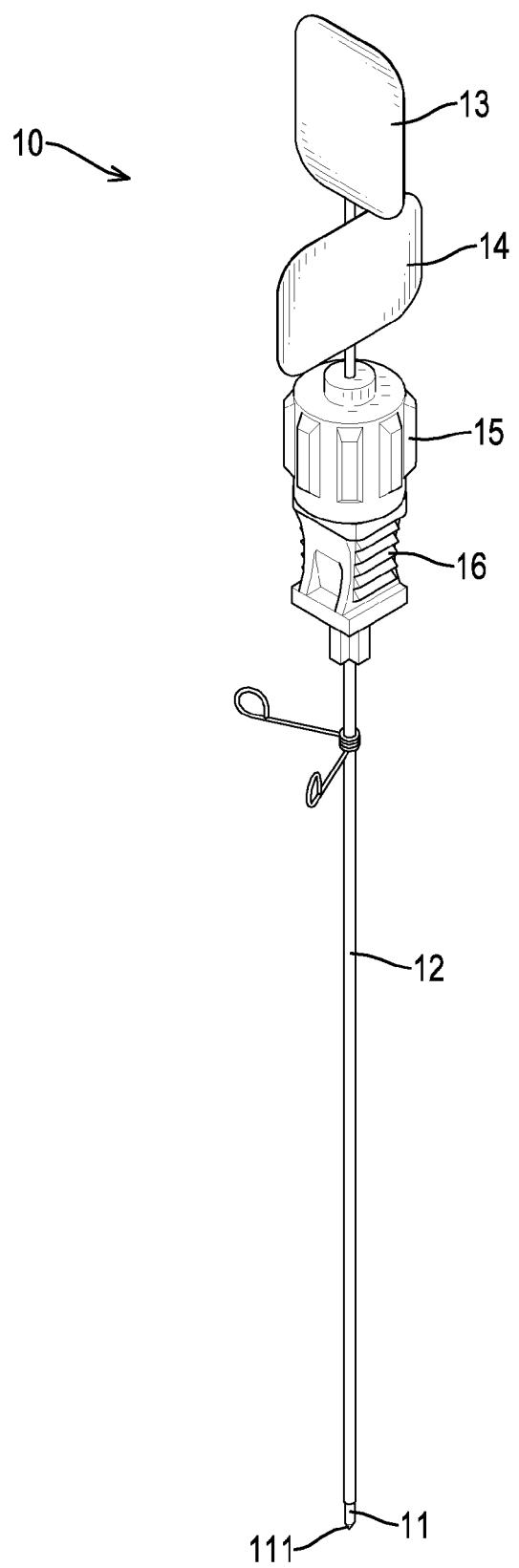
FIG. 1 is a perspective view of a first embodiment of a dual-wings percutaneous needle in accordance with the present invention.
Figure 2:
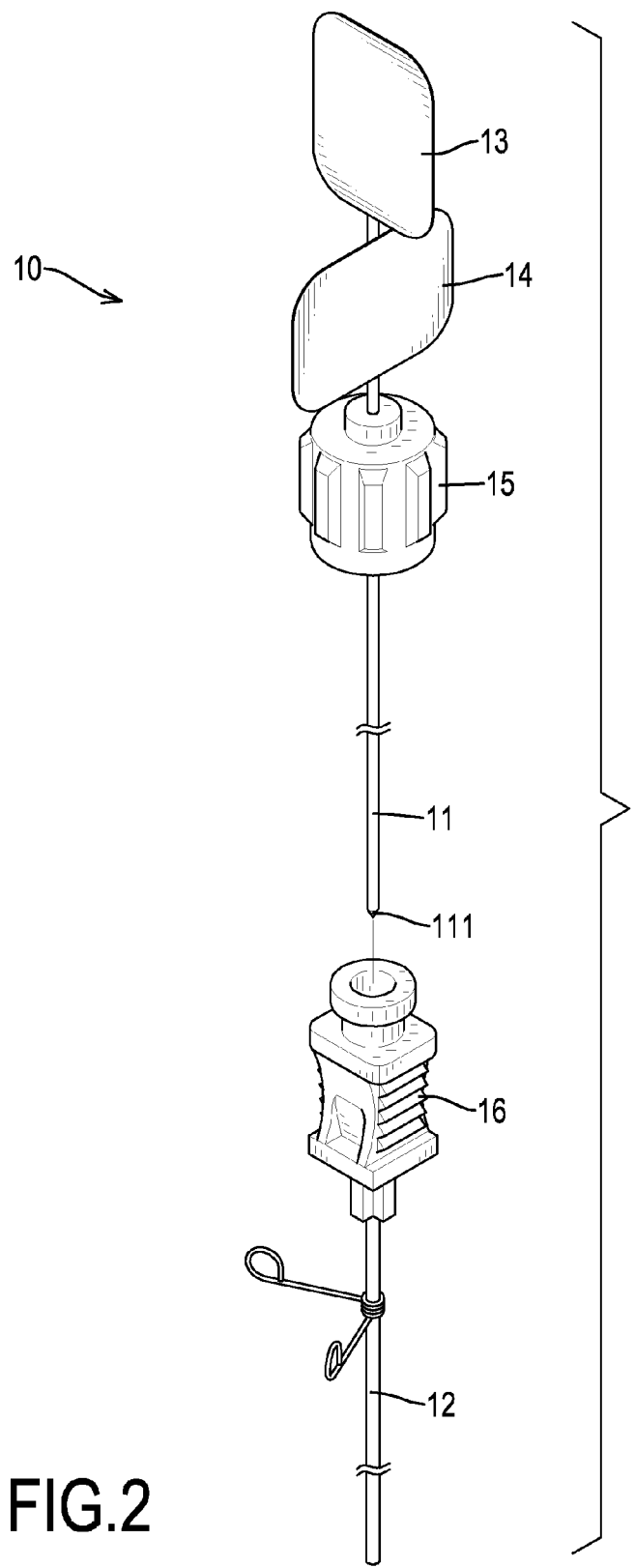
FIG. 2 is an exploded perspective view of the dual-wings percutaneous needle in FIG. 1.
Figure 4:
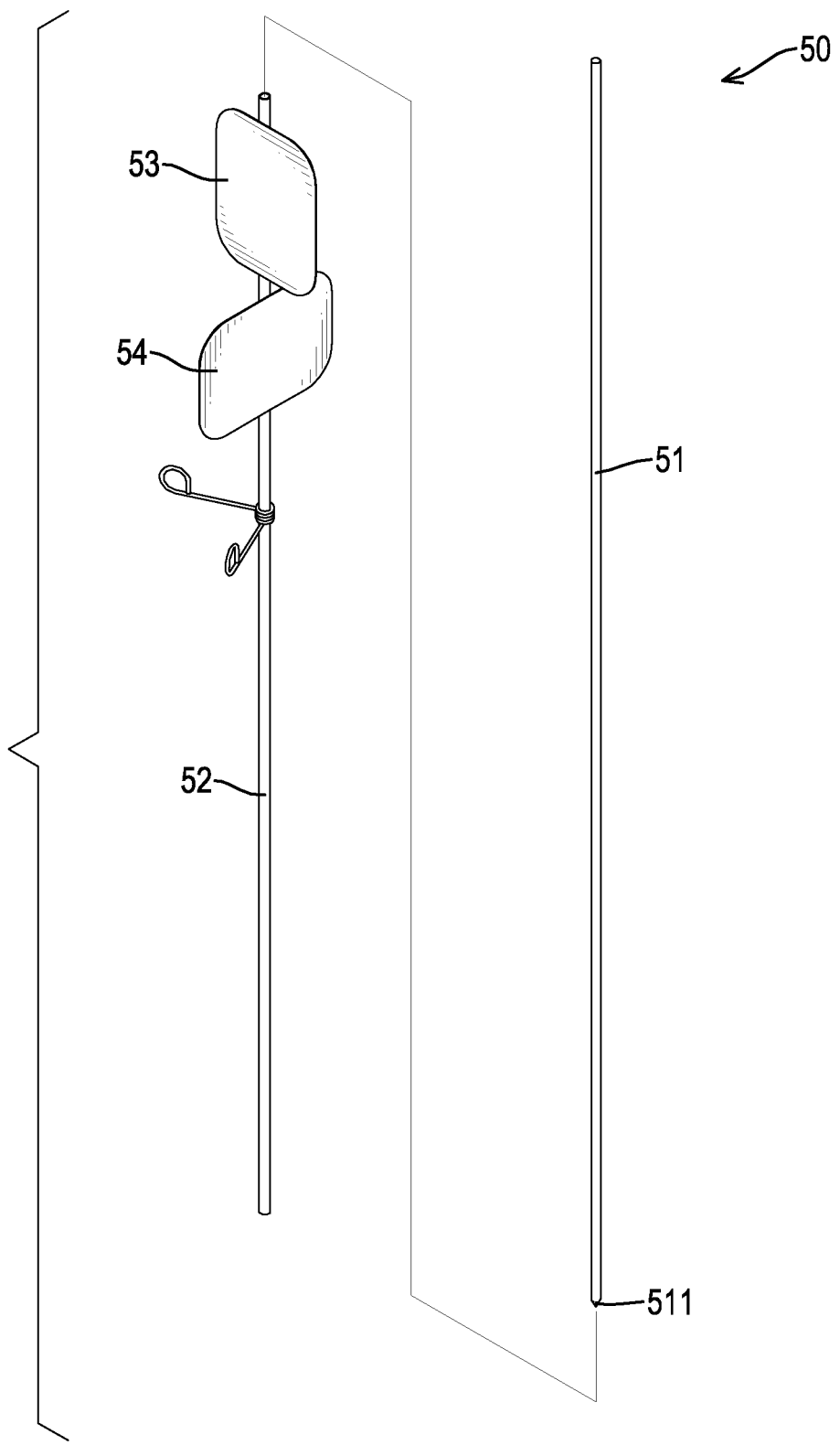
FIG. 4 is an exploded perspective view of a second embodiment of a dual-wings percutaneous needle in accordance with the present invention.
Figure 5:
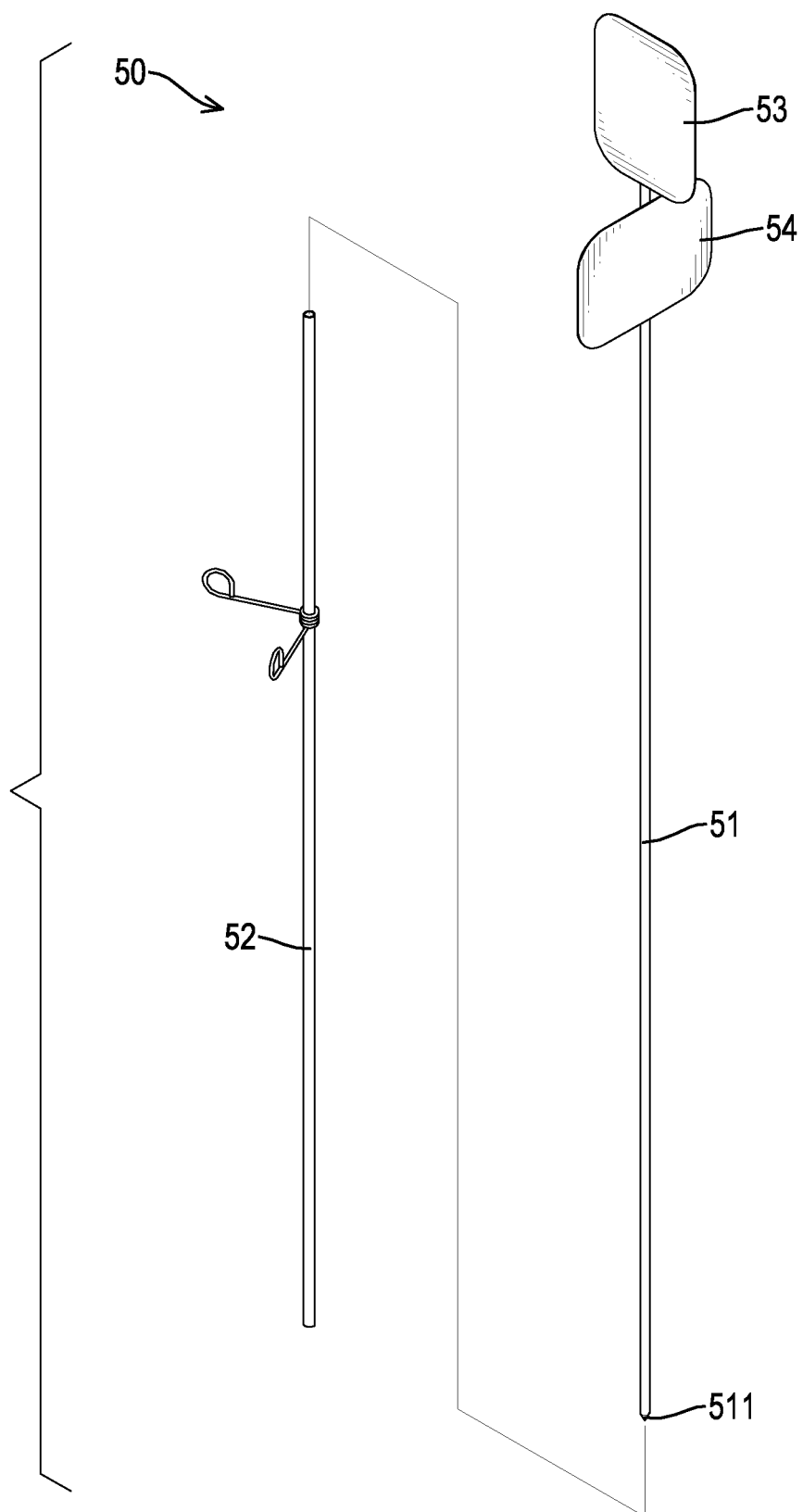
FIG. 5 is an exploded perspective view of a third embodiment of a dual-wings percutaneous needle in accordance with the present invention.

With reference to FIGS. 1, 4 and 5, a dual-wings percutaneous needle 10, 50 in accordance with the present invention comprises a sampling needle 11, 51, an outer needle 12, 52, a transverse position wing 13, 53 and a longitudinal position wing 14, 54.

The sampling needle 11, 51 has a lower end, an upper end, a diameter, a length, an external surface, a needle head 111, 511 and a mounting cover 15. The needle head 111, 511 is formed on the lower end of the sampling head 11, 51. The mounting cover 15 is mounted around the external surface of the sampling needle 11 near the upper end of the sampling needle 11.

The outer needle 12, 52 is a hollow metal pipe, is detachably mounted around the sampling needle 11, 51 and has a diameter, a length, a lower end, an upper end, an external surface and a locking mount 16. The diameter of the outer needle 12, 52 is larger than the diameter of the sampling needle 11, 51 to mount the sampling needle 11, 51 in the outer needle 12, 52. The length of the outer needle 12, 52 is shorter than the length of the sampling needle 11, 51 to allow the lower end of the sampling needle 11, 51 extending out of the lower end of the outer needle 12, 52. The locking mount 16 is mounted on the upper end of the outer needle 12 and is connected securely to the mounting cover 15 of the sampling needle 11 to hold the sampling needle 11 securely with the outer needle 12.

The transverse position wing 13, 53 is a sheet, is made of plastic and is mounted/adhered on the external surface of the sampling needle 11, 51 near the upper end of the sampling needle 11, 51 as shown in FIGS. 1 and 5 or is mounted/adhered on the external surface of the outer needle 52 near the upper end of the outer needle 52 as shown in FIG. 4.

The longitudinal position wing 14, 54 is a sheet, is made of plastic, is mounted/adhered on the external surface of the sampling needle 11, 51 adjacent to the transverse position wing 13, 53 and is perpendicular to the transverse position wing 13, 53 as shown in FIGS. 1 and 5 or is mounted/adhered on the external surface of the outer needle 52 adjacent to the transverse position wing 53 and is perpendicular to the transverse position wing 53 as shown in FIG. 4. In use, with reference to FIG. 3A, a laser angle guide assembly (not shown) is moved into a surgery room above a patient lies on a bed and generates a transverse laser beam 20 and a longitudinal laser beam 30. The laser beams 20, 30 are perpendicular to each other and emitted on the patient's body to form an alternating spot 40 at a desired position. At this time, the doctor or the user can hold and move the dual-wings percutaneous needle in accordance with the present invention to move the needle head 111 of the sampling needle 11 above the alternating spot 40. When the dual-wings percutaneous needle moves above the alternating spot 40, the laser beams 20, 30 will respectively project onto the position wings 13, 14.

Figure 3:
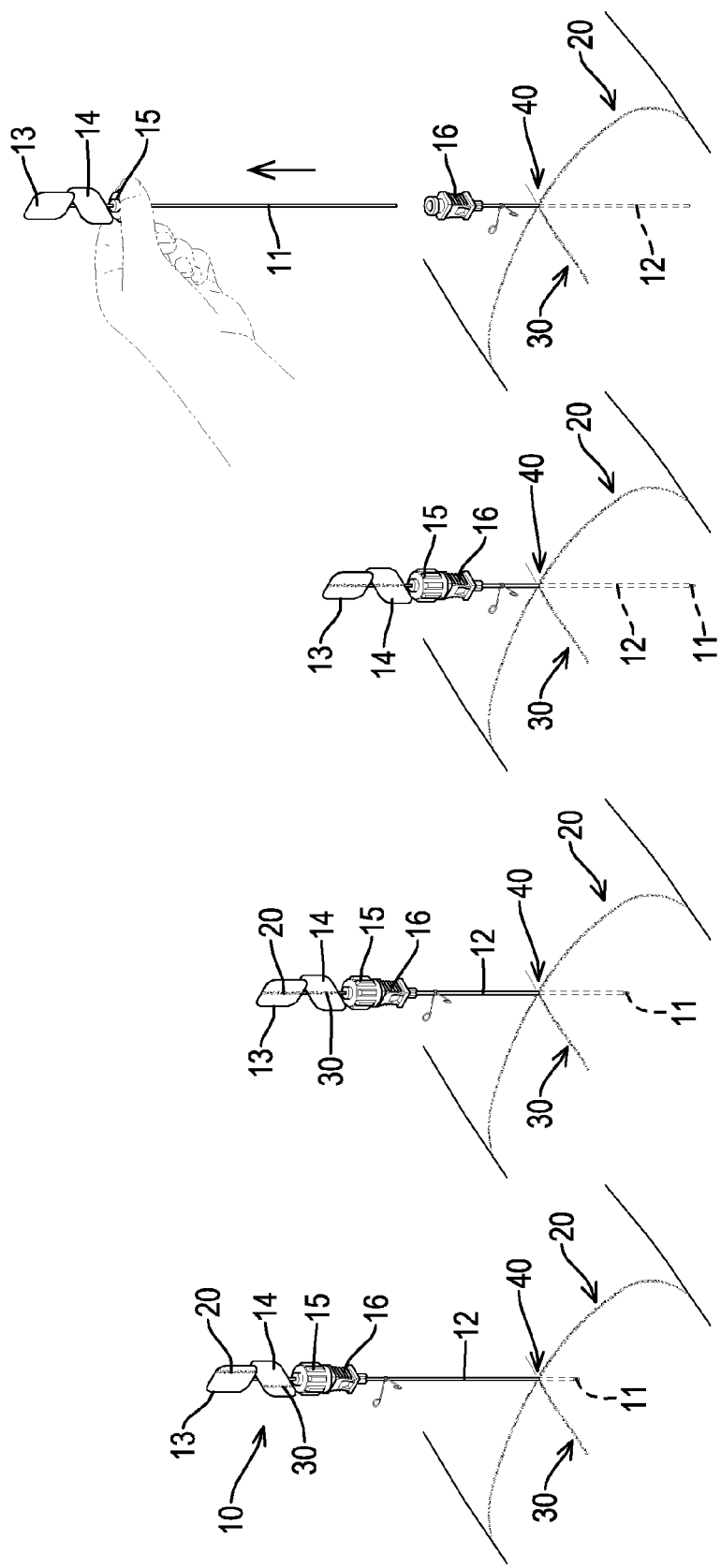
FIGS. 3A to 3D are operational views of the dual-wings percutaneous needle in FIG. 1.

If the needle head 111 of the sampling needle 11 is not perpendicular to the laser beams 20, 30 at the same time, the laser beams 20, 30 projected onto the position wings 13, 14 will not align with each other as shown in FIG. 3A. With the misalignment between the laser beams 20,30 and the positioning wings 13, 14, the puncturing angle of the needle head 111 of the sampling needle 11 has a deviation relative to the desired puncturing angle and may fail to take a specimen of tissue from the patient. With reference to FIG. 3B, the doctor or the user can adjust the puncturing angle of the needle head 111 of the sampling needle 11 to enable the laser beams 20, 30 to align with the position wings 13, 14. Then, the puncturing angle of the needle head 111 of the sampling needle 11 will fit in with the desired puncturing angle.

When the puncturing angle of the needle head 111 of the sampling needle 11 fits in with the desired puncturing angle, the doctor can plug deeply into the patient's body to enable the needle head 111 of the sampling needle 11 to take a specimen of tissue from the patient as shown in FIG. 3C. With reference to FIG. 3D, the doctor or the user can move the sampling needle 11 out of the patient's body by separating the mounting cover 15 from the locking mount 16 to check and analyze the specimen of tissue.

Accordingly, the dual-wings percutaneous needle in accordance with the present invention can be operated by adjusting the puncturing angle of the needle head 111 of the sampling needle 11 to enable the laser beams 20, 30 to align with the position wings 13, 14. Then, the puncturing angle of the needle head 111 of the sampling needle 11 will fit in with the desired puncturing angle to take a specimen of tissue from the patient precisely and easily to avoid causing pain and leading complications to the patient.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A dual-wing percutaneous needle comprising:
   a sampling needle having
      a lower end;
      an upper end;
      a diameter;
      a length;
      an external surface; and
      a needle head formed in the lower end of the needle;
   an outer needle being hollow, detachably mounted around the sampling needle and having
      a lower end;
      an upper end;
      an external surface;
      a diameter being larger than the diameter of the sampling needle to allow the sampling needle to mount in the outer needle; and
      a length being shorter than the length of the sampling needle to allow the lower end of the sampling needle to extend out of the lower end of the outer needle;
   a transverse position wing being lamellar and stuck on the external surface of the sampling needle near the upper end of the sampling needle; and
   a longitudinal position wing being lamellar, stuck on the external surface of the sampling needle, the longitudinal position wing being spaced from the transverse position wing at an interval along the length of the sampling needle, and the longitudinal position wing being perpendicular to the transverse position wing.

2. The dual-wing percutaneous needle as claimed in claim 1, wherein
   the sampling needle has a mounting cover mounted around the external surface of the sampling needle near the upper end of the sampling needle; and
   the outer needle has a locking mount mounted on the upper end of the outer needle and connected securely to the mounting cover of the sampling needle to hold the sampling needle with the outer needle.

3. A dual-wing percutaneous needle comprising:
   a sampling needle having
      a lower end;
      an upper end;
      a diameter;
      a length;
      an external surface; and
      a needle head formed in the lower end of the sampling needle;
   an outer needle being hollow, detachably mounted around the sampling needle and having
      a lower end;
      an upper end;
      an external surface;
      a diameter being larger than the diameter of the sampling needle to allow the sampling needle to mount in the outer needle; and
      a length being shorter than the length of the sampling needle to allow the lower end of the sampling needle to extend out of the lower end of the outer needle;
   a transverse position wing being lamellar and stuck on the external surface of the outer needle near the upper end of the outer needle; and
   a longitudinal position wing being lamellar, stuck on the external surface of the outer needle, the longitudinal position wing being to spaced from the transverse position wing at an interval along the length of the outer needle, and the longitudinal position wing being perpendicular to the transverse position wing.

* * * * *